(12) United States Patent
Holmstrom

(10) Patent No.: US 7,978,888 B2
(45) Date of Patent: Jul. 12, 2011

(54) SYSTEM AND APPERTAINING METHOD FOR STRUCTURED REPORTING OF A NATIVE MEASUREMENT IMPORT COUNT FOR DISPLAY

(75) Inventor: Eric Holmstrom, Dexter, MI (US)

(73) Assignee: Siemens Aktiengesellschaft, Munich (DE)

( * ) Notice: Subject to any disclaimer, the term of this patent is extended or adjusted under 35 U.S.C. 154(b) by 945 days.

(21) Appl. No.: 11/582,201

(22) Filed: Oct. 16, 2006

(65) Prior Publication Data

US 2008/0092035 A1   Apr. 17, 2008

(51) Int. Cl.
*G06K 9/00* (2006.01)

(52) U.S. Cl. .................................. 382/128; 715/234

(58) Field of Classification Search .................. 382/100, 382/128, 129, 130, 131, 132, 133, 134, 173, 382/181; 378/1, 37, 21, 41, 42, 38, 44, 51; 128/920; 600/300
See application file for complete search history.

(56) References Cited

U.S. PATENT DOCUMENTS

| | | | | |
|---|---|---|---|---|
| 2002/0169639 | A1* | 11/2002 | Yu | 705/3 |
| 2004/0207661 | A1* | 10/2004 | Akaki | 345/764 |
| 2005/0127891 | A1* | 6/2005 | Bae et al. | 324/72 |
| 2005/0192836 | A1* | 9/2005 | Rossinni et al. | 705/2 |
| 2006/0064328 | A1* | 3/2006 | Datta et al. | 705/3 |
| 2006/0072797 | A1* | 4/2006 | Weiner et al. | 382/128 |
| 2007/0008172 | A1* | 1/2007 | Hewett et al. | 340/870.38 |
| 2007/0109294 | A1* | 5/2007 | Gotman et al. | 345/418 |
| 2007/0176931 | A1* | 8/2007 | Tivig et al. | 345/440 |
| 2007/0248265 | A1* | 10/2007 | Lundstrom et al. | 382/168 |
| 2008/0215525 | A1* | 9/2008 | Kakimoto et al. | 707/1 |

OTHER PUBLICATIONS

Clunie, David A, DICOM Structured Reporting, 2000, PixelMed Publishing, ISBN 0-9701369-0-0, Chapters 1, and Annex D, pp. 29, 363-364. Available online at: http://www.pixelmed.com/srbook.html.*

* cited by examiner

*Primary Examiner* — Bhavesh M Mehta
*Assistant Examiner* — Tahmina Ansari
(74) *Attorney, Agent, or Firm* — Schiff Hardin LLP

(57) ABSTRACT

A method and appertaining system are provided for presenting observation and measurement data that is supplementary to a native mode application to a display. A DICOM Structured Report (SR) file is read into a database using one or more mapping files. An algorithm determines which values in the SR have mappings to the database defined using the mapping files, and values of the SR having defined mappings are imported into the database. Quantity values related to a count of data imported into the database are determined, and a display of a percentage and counts of those values are provided on a display to a user.

10 Claims, 4 Drawing Sheets

SYSTEM AND APPERTAINING METHOD FOR STRUCTURED REPORTING OF A NATIVE MEASUREMENT IMPORT COUNT FOR DISPLAY

BACKGROUND

The invention relates to a system and appertaining method for providing a structured reporting of a native measurement import count for display to a user.

A need previously existed in the medical community to provide standards with respect to sharing information related to digital imaging and communication of associated data. The Digital Imaging and Communication in Medicine (DICOM) is a global information technology standard that is used in virtually all hospitals worldwide. Its current structure, which was developed in 1993, is designed to ensure the interoperability of systems used to: Produce, Store, Display, Process, Send, Retrieve, Query or Print medical images and derived structured documents as well as to manage related workflow.

DICOM Structured Reporting (SR) is used for sharing observations and measurements made on studies with other DICOM devices such as a diagnostic workstation. DICOM Structured Reports may be created by a number of medical devices such as diagnostic workstations and acquisition products to name the most common. The basic goal of SR objects is to share measurement, calculation, and in some cases report information created with other vendors in a standard format. Because the format is standard, other vendors supporting the importing of SR data or display of SR data can easily implement support making life easier for the physician and less work for the physician to re-do measurements or manually copy and paste measurements into a proprietary software product.

Although the information is defined and communicated according to the DICOM standard, often users do not actually know the extent of data being shared and imported into a native system (a system designed to accept and process DICOM data) for a specific use. Furthermore, users have little understanding of the possibility of performing further calculation and analysis on collected data outside of the context of a specific application designed to work with a specific piece of diagnostic equipment. Currently, the user is relegated to simply displaying obtained measurements from a piece of diagnostic equipment with a proprietary viewer designed to work with the diagnostic equipment.

At present, there are no products that provide access to information related to the DICOM data that has been collected outside of the context of the native application provided by the supplier of related equipment.

Outside of the native applications that specifically handle DICOM data from a particular piece of diagnostic equipment, applications exist that show the raw/basic DICOM measurement data in, e.g., Microsoft Word or Adobe PDF format, but such applications simply provide a display of the data in a disorganized manner or simply in the order that they were supplied in the DICOM Structured Report SR by the measurement device. The measurement data are not applied to any further analysis, i.e., in an automated measurement analysis created from measurements intended for appertaining systems. Additionally, such further analyzed data are not applied to any final report or output of the native system that the data were entered into.

SUMMARY

It is possible to provide a further analysis and processing on the DICOM data outside of the context that the data was originally intended for, and it is further possible to integrate such data on a display along with the display of the native system. By way of an example, the DICOM data can be analyzed for information such as percentages and counts of observations/measurements imported natively into a DICOM system of review.

It is possible, with the DICOM data, to provide a display of additional information related to the DICOM data, such as the count of measurements that are actually imported into a native application or database for which the DICOM data was originally intended, or to subject the DICOM data to further calculations or process this data for general use.

By providing additional processing of the DICOM data outside of the context of the native application, and further by providing a separate or integrated display of the results of this additional processing, the full potential of the data collected can be realized. The invention could advantageously be utilized by anyone involved in leading-edge technology, particularly those interested in products related to the Integrated Healthcare Enterprise (IHE), which is an initiative by healthcare professionals and industry to improve the way computer systems in healthcare share information. Many modalities support the sharing of measurements and observations. DICOM defines templates to correctly share measurements, and IHE further promotes the sharing of these measurements.

Accordingly, an inventive method is provided for presenting observation and measurement data that is supplementary to a native mode application to a display, comprising: reading a DICOM Structured Report (SR) file into a database using one or more mapping files; determining which values in the SR have mappings to the database defined using the mapping files; importing values of the SR having defined mappings into the database; determining quantity values related to a count of data imported into the database; and providing a display of a percentage and counts of those values on a display to a user. According to an embodiment, the values are selected from the group consisting of a number of measurements supported by a native mode system, a number of imported measurements, and a percentage of imported measurements. The method may further comprise opening a study associated with the SR; and triggering the determining of quantity values automatically by the opening of the study. The method may further comprise determining an originating device used for the SR; and displaying a product name associated with the originating device. The providing of the display may comprise: overlaying on the display the percentage and counts on the image data without embedding it into stored pixel data prior to display, may comprise displaying a pop-up window containing the percentage and counts, or could simply provide the information in a separate area of the display.

Furthermore, an inventive system is provided for presenting observation and measurement data that is supplementary to a native mode application comprising: a medical apparatus that produces DICOM SR data; mapping files comprising mapping information that maps SR data into a database; an algorithm that determines which values in the SR have mappings to the data base utilizing the mapping files and imports values of the SR having defined mappings into the database and determines quantity values related to a count of data imported into the database; and a user display upon which the algorithm provides percentage and count information of the values.

DESCRIPTION OF THE DRAWINGS

The invention is illustrated below by way of reference to various preferred embodiments illustrated in the drawings and appertaining related discussion.

DETAILED DESCRIPTION OF THE PREFERRED EMBODIMENTS

Figure 1:
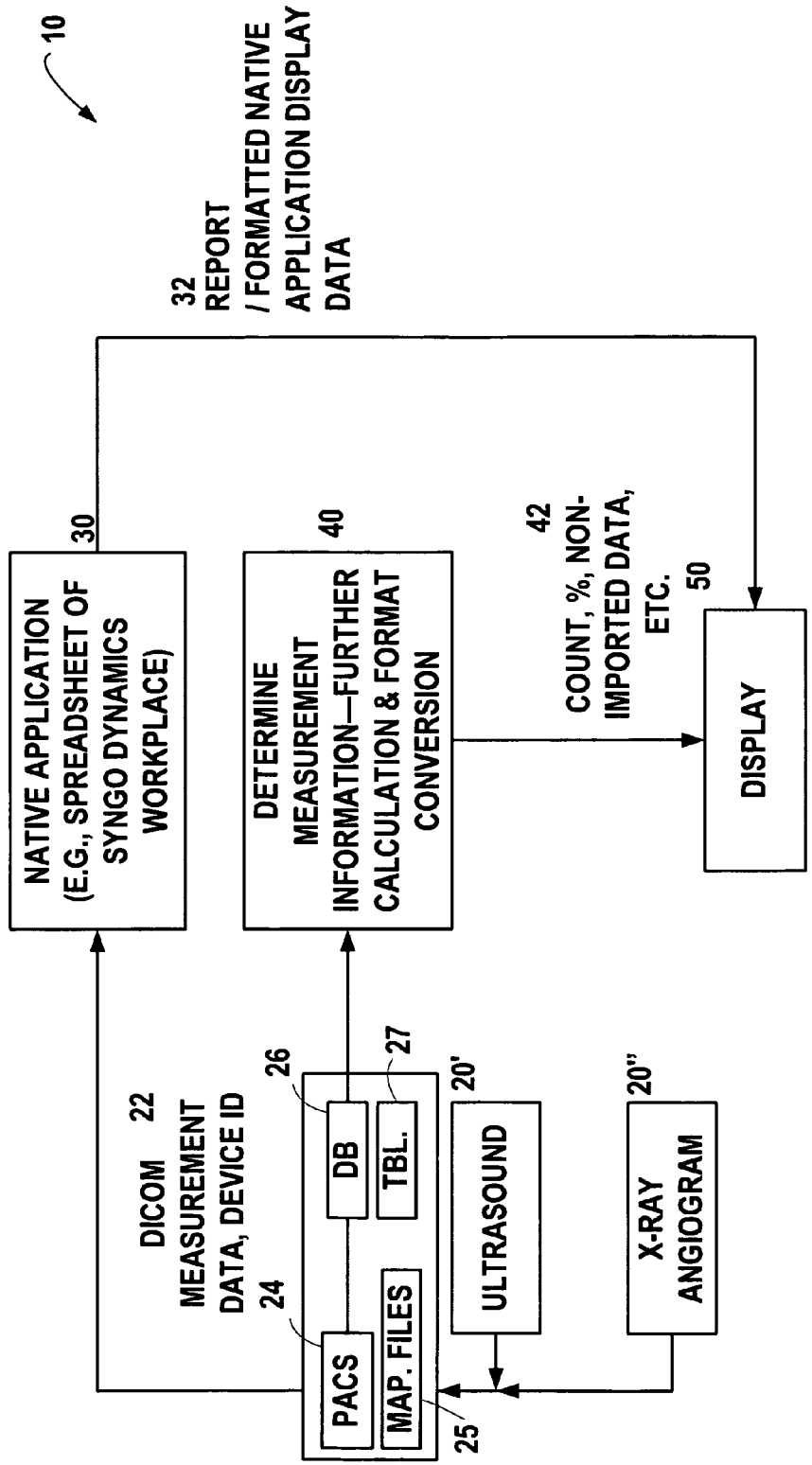
FIG. 1 is a basic block diagram showing the components of the system.

FIG. 1 is a block diagram of the basic system 10 that is used for providing additional analysis of generated data, Accordingly, DICOM measurement data 22 is produced by an apparatus, such as an ultrasound (US) machine 20' or X-Ray Angiographic/Cath (XA) machine 20" (collectively 20). This data 22 is provided to a native application 30 that is specifically designed to process the DICOM data in a particular way and format the data for presenting on a display 50.

The data 22, however, can further be provided to a system or process 40 that analyzes the DICOM data 22 outside of the context of a native application 20 for the particular machine or modality 20.

By way of example, the analytical process 40 could make an analysis about the amount of data that was imported into the native application 30 and provide resultant statistics 42 to the user. A table 27 exists in the database 26 of the application with the measurements that are mapped. There might be, for example, fifty rows in that table 27, but only twenty-five rows might actually have values. Thus, 50% of all possible mapped measurements were imported for the acquisition device that created the series of images. Also, the count of twenty-five could be provided to the user too.

Figure 4:
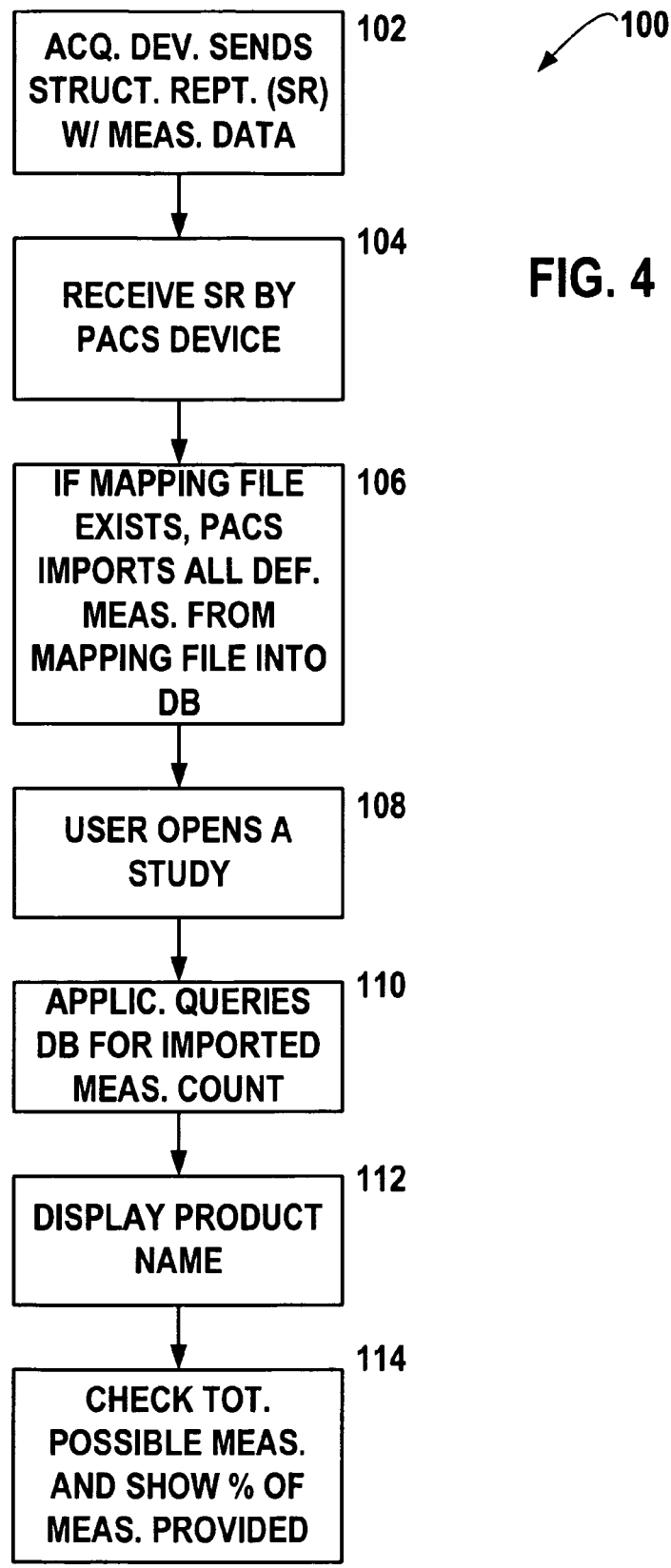
FIG. 4 is a flowchart illustrating a procedure according to an embodiment of the invention.

The steps in this procedure could include, as illustrated in FIG. 4: 1) the acquisition device 20 sends an SR with measurement data 102; 2) the receiving PACS device 24, 104 determines if a mapping file 25 exists for the acquisition that just created the series of images 106 and if one does, then 3) the receiving PACS device 24 imports all defined measurements from a mapping file 25 for that acquisition device 20 into the database 26, 106; 4) the user opens a study 108 which automatically triggers the application 40 to query the database 26 in order to get a count of measurements imported for that series of images and display it 110, check which vendor product mapping file 25 was used and display the product name for product context 112, and also checks for the total of possible measurements compared to the actual count from above to show a percentage of the measurements that actually were provided by that modality 114.

Figure 2:
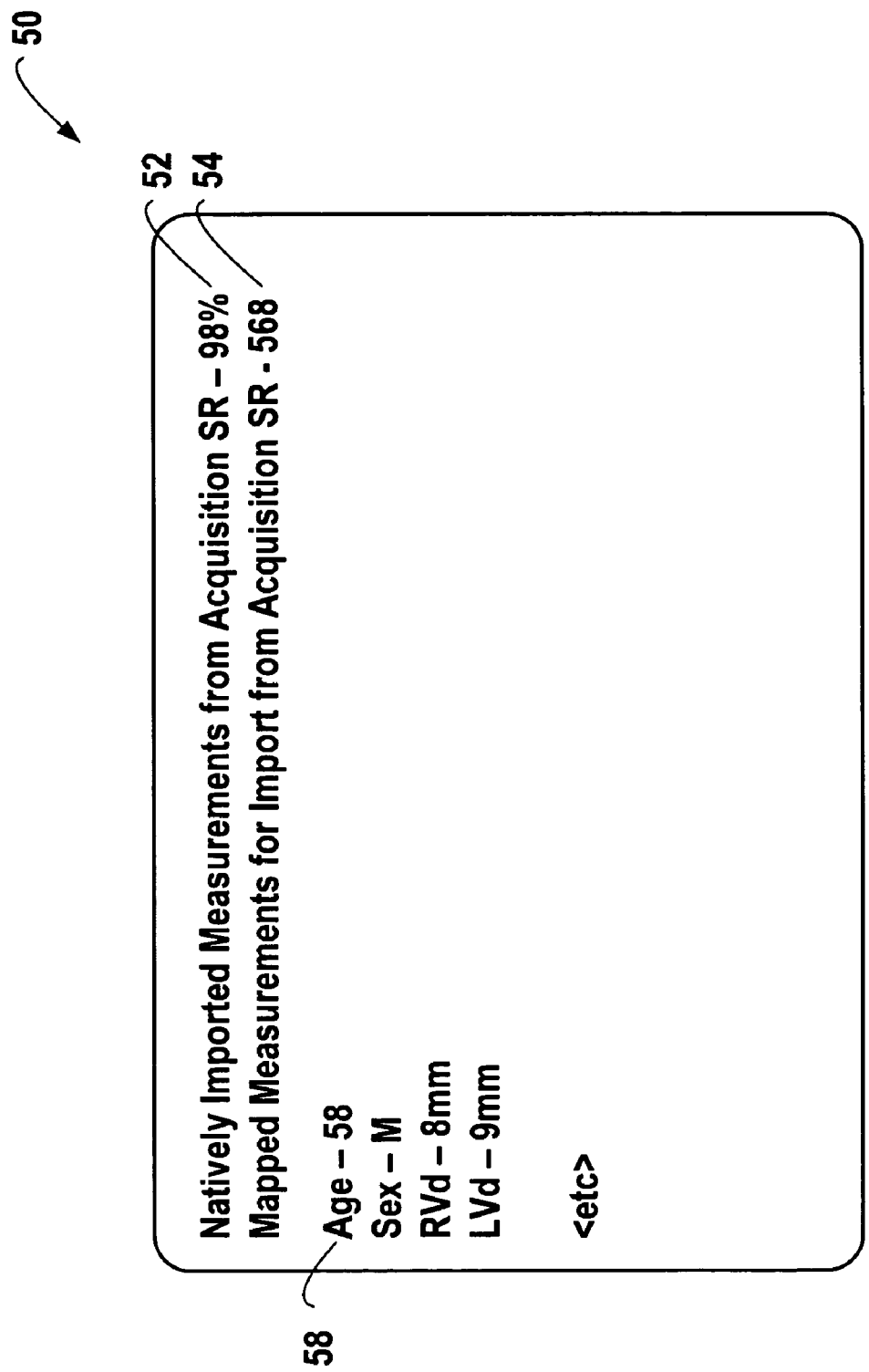
FIG. 2 is a simplified exemplary screen shot of information produced.

FIG. 2 illustrates an exemplary display 50 that could be provided to a user. The display 50 indicates that in a given application 98% of the measurements 22 were natively imported into the native application 30 from the acquisition structured report (SR) 52. It further indicates that 568 measurements 22 were mapped for import from the acquisition SR 54.

"Mapped for import" can be explained as follows. Each vendor acquisition product may share its measurements and observations in a slightly different manner. Therefore, in order to be accurate on the display of those measurements, testing needs to be done between the vendor acquisition product and the display product to make sure the values provided from that acquisition are shown correctly in the appropriate places on the display product. Because SR styles vary and each acquisition product might label things a little differently than the other acquisition products, special mapping files need to be created that are polled by the PACS receiving the SR data each time a study comes in.

So for a given series of images, one mapping file or file set will be polled in order to determine where in the database and which values provided by the acquisition will be imported for later review at a display. Additional information 58 could be analyzed and presented on the display 50. What the percentages and counts can tell the user is that more data could have been supplied from that acquisition device . . . that not all of the possible data that mappings exist for was provided by the acquisition device. This might promote the use of the display tools to fill in the gaps for the missing measurements. As noted previously, this information could be provided separately from that produced by the native application 30 or could be combined in some format on the user's display 50.

By way of a further example, the display 50 could provide:

Measurements and Observations Natively Imported- 130/150 (87.5%) out of 160 mapped for this acquisition device and the Adult Echo template or Acquisition Generated Measurements and Observations Imported- 148/163 out of 160 mapped for this acquisition device As noted above, the display 50 could also possibly list the originating device 20 itself in the message if possible or if readable from the objects or database Providing visualization of the actual data being shared between applications promotes the aims of the IHE, visualizations such as a count or percentage of observations and measurements imported natively to improve workflow. For example, 87.5% of measurements may have been mapped into worksheets on a reporting system (e.g., the Syngo Dynamics Workplace reporting system) without the need for a user to have to reenter them. Advantageously, this can result in greater productivity, and the accuracy and amount of imported or mapped data can be easily verified. Furthermore, data that has not been imported can still be displayed to a user in, e.g., a separate viewer, for reference.

Thus, the present invention goes beyond simply presenting all data in a simple viewer—rather, the present invention maps the data for further calculations and thereby minimizes a requirement for a medical professional to utilize basic copy/paste techniques in order to get data into a proprietary medical system. So, with regard to the exemplary process above, the display application has various fields defined which represent those measurement and observation rows from the database for a series of images. For example, the worksheet might have a field defining an age having a value of 54. The value of 54 was obtained from a query to the database for the age variable in the list of measurements for this series of images.

The following example illustrates this concept. An ultrasound study arrives from the acquisition device 20' at the PACS 24 and is viewed at a post processing or reporting workstation. The doctor opens the study at the workstation and enters his calculations and observations worksheet to view measurements created at the acquisition instead of looking directly on each image. The doctor views a small label on his worksheet stating that 95% of possible calculations/observations mapped for the acquisition device of this study have been natively imported. There are a number of reasons, usually customer dependent, that all of the data is not imported. For example, a doctor is looking at a baby's heart and therefore does not care about the head area, so he provides a number of heart measurements, but no head measurements, in a particular, e.g., OB study.

The doctor can also determine that this calculation is true because many of his measurement fields are already populated without the need for him to look and/or copy and paste them to the worksheet. This is advantageous over the prior art that does not use SR, in which images are captured at an acquisition device and, in the pixel data itself, are embedded measurement values. The doctor would visually see these images and the embedded measurements and then hand type them into the appropriate fields in the worksheet on the display application. Some applications provide an unsightly dump of the SR data in a tree-node structure that is viewable to the doctors allowing them to copy values and then go to the worksheet and paste them in. Advantageously, with the present invention, the doctor has to visually look at less and do less manual entry for measurements and observations. The present embodiments do not need to embed the displayed ultrasound data information into the stored pixel data, but can present it on the fly to the user.

Returning to the example described above, the doctor also notes a label stating that 90% of the calculations/observations provided via the DICOM SR have been natively mapped into his worksheet for him automatically.

PRACTICAL EXAMPLE

Figure 3:
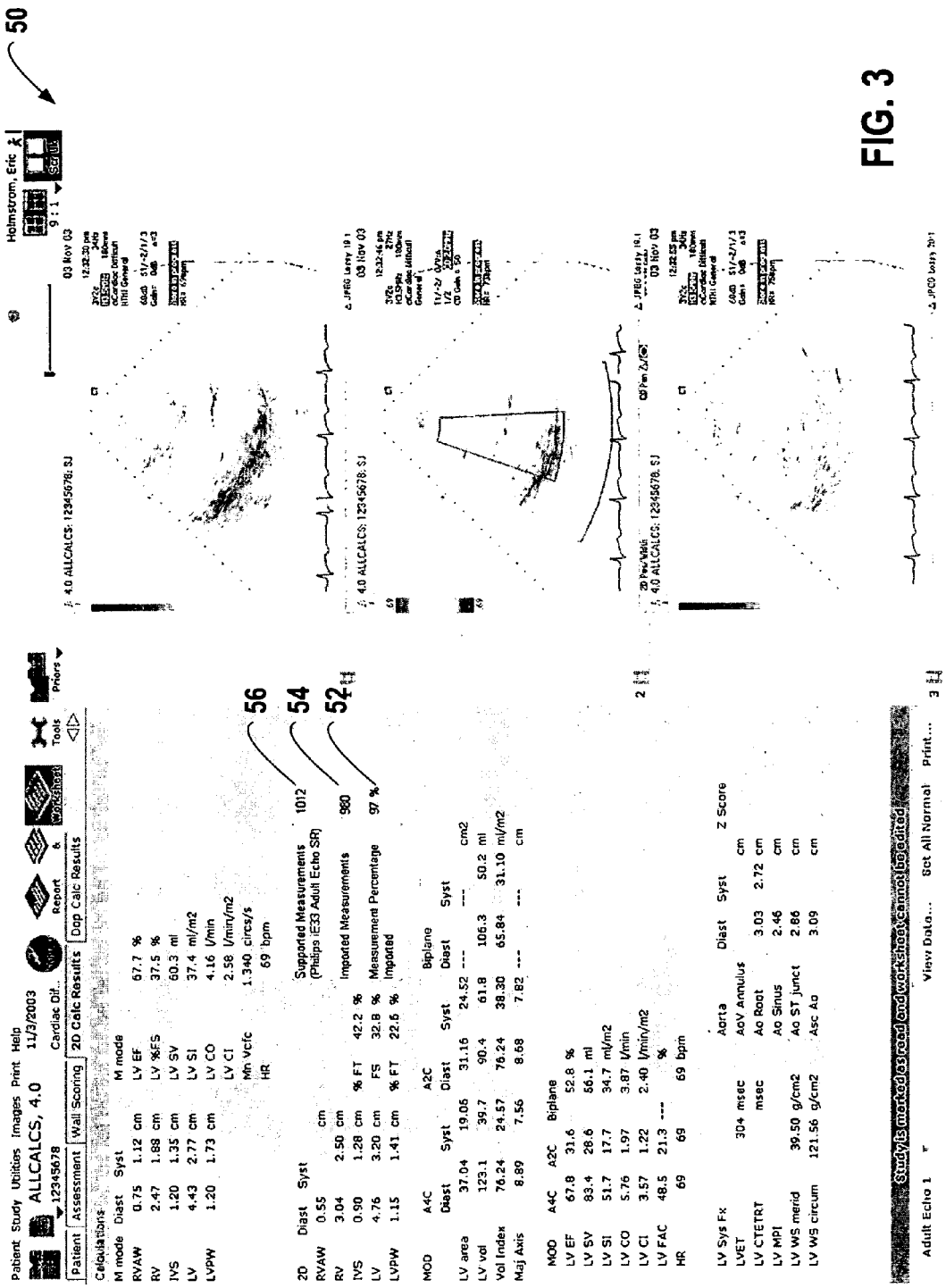
FIG. 3 is a real-life exemplary screen shot of the information produced.

FIG. 3 provides a real-life illustration of the invention in operation. A Philips Ultrasound product, called the iE33, supports the creation of Adult Echo Structured Reports. During a study on patient A, a Sonographer may be making measurements on the iE33 for the patient's heart during a rest period. These measurements are all recorded by the iE33 for later archiving or exporting of the study to another DICOM device on the network. When the study is exported, a number of images may be sent as well as a non-image object (the Structured Report).

The receiving DICOM device, e.g., a PACS, that has the ability to import the standard measurements and perhaps even some private measurements can then automatically map these measurements into the appropriate places on its system. When a physician reviews the study at the diagnostic workstation and wants to reference measurements while she does her reporting, then the measurement data will already be there—there is no need for the physician to manually look at each measurement on the image captures and then hand type them into the workstation software.

When a mapping file or mapping system is in place for reading measurements from the SR provided by the acquisition product and entering the measurement data into the proprietary system's place for those measurements, it can be assumed that a count of the supported measurements is known.

By simply using the count of supported measurements, the proprietary software can display: the number of supported measurements from that particular product's SR, the percentage of measurements imported from the SR(s) for a given study, the number of measurements and number of calculations separately or together that were imported from the SR(s) for a given study.

The application could be implemented as a library (DLL) that takes the SR and then parses the data and imports the supported or mapped data into the database for that particular series of images or study. However, the application is not limited to this implementation. For example, an executable program such as a DICOM SCP (Service Class Provider) might have the code written into it to do the same functions as the DLL. The DLL or DLL's could be considered as a DICOM SR Toolkit. A vendor could implement their own DICOM SR Toolkit which could be shared across any number of products. The SR Toolkit (DLL's) would be called by the DICOM SCP which is listening for study data when new study data arrives.

This behavior, once implemented, can be shared across all mapping systems for SR import across all vendors. As illustrated in FIG. 3, the display 50 comprises a region for displaying, e.g., a measurement percentage imported 52, the number of imported measurements 54, and the supported measurements 56, which in this case, related to the Philips iE33 Adult Echo SR. Although each vendor is likely to have a different implementation for the display, the general concept applies across all vendor implementations. The measurement counts and percentages do not need to be listed on the worksheet or screen with the measurements: they may also be listed on a list of studies in a simple column stating that measurements were imported and what the counts are. This could even be achieved via a pop up window when the user puts his mouse over the study in the list.

Although the primary exemplary applications described above focus on measurement counts and percentages, the system could be utilized to track the real-time average of the percentage of measurements imported. By way of example, if three studies were done, and each one had the following measurement percentages imported:

1. 25/50 measurements Philips iE33
2. 25/50 measurements Philips iE33
3. 35/50 measurements Philips iE33

Then the display software could conclude that on average only 56% of possible measurements are imported from a specific device. The software could go further and determine the averages across all devices which have imported SR data (non-specific vendors)

1. 25/50 measurements Philips iE33
2. 25/50 measurements GE VIVID 7
3. 35/50 measurements Philips iE33

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A method for presenting observation and measurement data that is supplementary to a native mode application processing DICOM Structured Report (SR) format to a display, comprising:
    producing a DICOM SR file containing data items in a medical apparatus;
    reading said DICOM SR file into a database using one or more mapping files comprising mapping information that maps the data items into the database, said mapping information being specific to said medical apparatus;
    determining which data items in the SR have mappings to the database defined using the mapping files;
    importing the data items of the SR that have defined mappings into the database;
    counting the data items of the SR that are imported into the database in said importing step; and
    displaying the count of the data items imported in said importing step and displaying a percentage of the data items in the SR that were imported in said importing step relative to the number of data items in the SR presented for importing during said importing step, said displaying step being performed on a display to a user.

2. The method according to claim 1, wherein said step of counting includes counting data items selected from the group consisting of a count of a number of measurements supported by a native mode system, a count of a number of imported measurements, and a percentage of imported measurements.

3. The method according to claim 1, further comprising:
    opening a study associated with the SR; and
    triggering said counting step automatically by the opening of the study.

4. The method according to claim 1, further comprising:
    determining an originating device used for the SR; and
    displaying a product name associated with the originating device.

5. The method according to claim 1, wherein the step of displaying includes:
    overlaying on the display the percentage and counts on the image data without e bedding it into stored pixel data prior to display.

6. The method according to claim 1, wherein the step of displaying includes:
    displaying a pop-up window containing the percentage and counts.

7. The method according to claim 6, wherein the step of displaying the pop-up window is triggered by moving a pointing device over a study displayed in a list of studies.

8. The method according to claim 1, further comprising:
    tracking in real-time an average of a percentage of data items imported.

9. A system for presenting observation and measurement data that is supplementary to a native mode application processing DICOM Structured Report (SR) format comprising:
    a medical apparatus that produces DICOM SR (Structured Report) data;
    mapping files comprising mapping information that maps SR data into a database, said mapping information being sufficient to said medical apparatus;
    an algorithm that determines which data items in the SR have mappings to the data base utilizing the mapping files and imports the data items of the SR having defined mappings into the database and determines a count of the data items imported into the database, said algorithm determining a percentage of the data items imported into the database relative to the data items present in the SR and presented for importing; and
    a user display upon which the algorithm provides percentage and count information.

10. A system as claimed in claim 9. wherein said percentage and count information includes percentage and count information of measurement Values mapped into the database.

* * * * *